US012649916B2

(12) United States Patent
    Fordham

(10) Patent No.:    US 12,649,916 B2
(45) Date of Patent:         Jun. 9, 2026

(54) METHOD FOR SELECTING POLYNUCLEOTIDES BASED ON THE SIZE IN A GLOBULAR FORM

(71) Applicant: Oxford Nanopore Technologies PLC, Oxford (GB)

(72) Inventor: Daniel George Fordham, Oxford, GA (US)

(73) Assignee: Oxford Nanopore Technologies PLC, Oxford (GB)

( * ) Notice: Subject to any disclaimer, the term of this patent is extended or adjusted under 35 U.S.C. 154(b) by 857 days.

(21) Appl. No.: 17/057,164

(22) PCT Filed: May 24, 2019

(86) PCT No.: PCT/GB2019/051441
    § 371 (c)(1),
    (2) Date: Nov. 20, 2020

(87) PCT Pub. No.: WO2019/224558
    PCT Pub. Date: Nov. 28, 2019

(65) Prior Publication Data
    US 2021/0198656 A1      Jul. 1, 2021

(30) Foreign Application Priority Data
    May 24, 2018    (GB) ..................................... 1808556

(51) Int. Cl.
    *C12N 15/10*        (2006.01)
    *C12Q 1/6806*       (2018.01)
    *C12Q 1/6869*       (2018.01)
(52) U.S. Cl.
    CPC ....... *C12N 15/1017* (2013.01); *C12Q 1/6806* (2013.01); *C12Q 1/6869* (2013.01)

(58) Field of Classification Search
    None
    See application file for complete search history.

(56) References Cited

U.S. PATENT DOCUMENTS 7,527,929 B2    5/2009   McKernan et al.
9,783,799 B2    10/2017  Kim et al.
(Continued)

FOREIGN PATENT DOCUMENTS

WO      WO 1998/05767 A1      2/1998
WO      WO 2000/028312 A1     5/2000
(Continued)

OTHER PUBLICATIONS

Xuan et al., "Size separation of biomolecules and bioparticles using micro/nanofabricated structures" Analytical Methods vol. 6 pp. 27-37 DOI: 10.1039/c3ay41364k (Year: 2014).*
(Continued)

*Primary Examiner* — Eric Olson
(74) *Attorney, Agent, or Firm* — Wolf, Greenfield & Sacks, P.C.

(57)                    ABSTRACT

The invention provides methods of selecting polynucleotides based on their size in globular form. The polynucleotides may be treated with a condensation medium. e.g. comprising polyethylene glycol. e.g. PEG8000, and salt, in order to adopt a globular form. The method may employing filtering in order to retain the larger nucleic acids and make the larger nucleic acids available for sequencing applications, such as nanopore sequencing. The invention also relates to kits for selecting polynucleotides.

15 Claims, 3 Drawing Sheets

(56)          References Cited

U.S. PATENT DOCUMENTS

| | | |
|---|---|---|
| 2002/0106686 A1 | 8/2002 | McKernan |
| 2002/0110829 A1 | 8/2002 | Kolzau et al. |
| 2009/0275486 A1 | 11/2009 | Kurn et al. |
| 2017/0136433 A1 | 5/2017 | Sun et al. |

FOREIGN PATENT DOCUMENTS

| | | |
|---|---|---|
| WO | WO 2006/083721 A2 | 8/2006 |
| WO | WO 2006/100484 A2 | 9/2006 |
| WO | WO 2007/092313 A2 | 8/2007 |
| WO | WO 2008/102120 A1 | 8/2008 |
| WO | WO 2009/077734 A2 | 6/2009 |
| WO | WO 2010/086602 A1 | 8/2010 |
| WO | WO 2010/122293 A1 | 10/2010 |
| WO | WO 2011/067559 A1 | 6/2011 |
| WO | WO 2012/107778 A2 | 8/2012 |
| WO | WO 2012/164270 A1 | 12/2012 |
| WO | WO 2013/057495 A2 | 4/2013 |
| WO | WO 2013/083983 A1 | 6/2013 |
| WO | WO 2013/098561 A1 | 7/2013 |
| WO | WO 2013/098562 A2 | 7/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/135838 A1 | 9/2014 |
| WO | WO 2015/055981 A2 | 4/2015 |
| WO | WO 2015/150786 A1 | 10/2015 |
| WO | WO 2015/166275 A1 | 11/2015 |
| WO | WO 2016/034591 A2 | 3/2016 |
| WO | WO 2016/055777 A2 | 4/2016 |
| WO | WO 2016/061556 A1 | 4/2016 |
| WO | WO 2016/132123 A1 | 8/2016 |
| WO | WO 2017/041013 A1 | 3/2017 |
| WO | WO 2019/006321 A1 | 1/2019 |

OTHER PUBLICATIONS

Ramos et al., "DNA ψw-Condensation and Reentrant Decondensation: Effect of the PEG Degree of Polymerization" J Phys Chem B vol. 109 pp. 23661-23665 (Year: 2005).*

Endres et al., "Evaluation of an ion-exchange membrane for the purification of plasmid DNA" Biotechnol Appl Biochem vol. 37 pp. 259-266 (Year: 2003).*

Yang et al., "Advances in Nanopore Sequencing Technology" Journal of Nanoscience and Nanotechnology vol. 13 p. 4521-4538, doi: 10.1166/jnn.2013.7756 (Year: 2013).*

Mizuno et al., "Manipulation of a Large DNA Molecule using the Phase Transition" Journal of Biological Physics vol. 28 pp. 587-603 (Year: 2002).*

United Kingdom Search Report for Application No. GB1808556.3 mailed Feb. 6, 2019.

International Search Report and Written Opinion for International Application No. PCT/GB2019/051441 mailed Aug. 5, 2019.

International Preliminary Report on Patentability for International Application No. PCT/GB2019/051441 mailed Dec. 3, 2020.

Altschul et al., Basic local alignment search tool. J Mol Biol. Oct. 5, 1990;215(3):403-10. doi: 10.1016/S0022-2836(05)80360-2.

Altschul, A protein alignment scoring system sensitive at all evolutionary distances. J Mol Evol. Mar. 1993;36(3):290-300. doi: 10.1007/BF00160485.

Braha et al., Designed protein pores as components for biosensors. Chem Biol. Jul. 1997;4(7):497-505. doi: 10.1016/s1074-5521(97)90321-5.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Devereux et al., A comprehensive set of sequence analysis programs for the VAX. Nucleic Acids Res. Jan. 11, 1984;12(1 Pt 1):387-95. doi: 10.1093/nar/12.1part1.387.

Heron et al., Simultaneous measurement of ionic current and fluorescence from single protein pores. J Am Chem Soc. Feb. 11, 2009;131(5):1652-3. doi: 10.1021/ja808128s.

Hirano et al., Sizing of single globular DNA molecules by using a circular acceleration technique with laser trapping. Anal Chem. Jul. 1, 2008;80(13):5197-202. doi: 10.1021/ac8003538. Epub May 20, 2008.

Holden et al., Direct introduction of single protein channels and pores into lipid bilayers. J Am Chem Soc. May 11, 2005;127(18):6502-3. doi: 10.1021/ja042470p.

Katsura et al., Manipulation of globular DNA molecules for sizing and separation. Electrophoresis. Jan. 2000;21(1):171-5. doi: 10.1002/(SICI)1522-2683(20000101)21:1<171::AID-ELPS171>3.0.CO;2-U.

Kranz et al., High precision genome sequencing of engineered Gluconobacter oxydans 621H by combining long nanopore and short accurate Illumina reads. J Biotechnol. Sep. 20, 2017;258:197-205. doi: 10.1016/j.jbiotec.2017.04.016. Epub Apr. 19, 2017.

Langecker et al., Synthetic lipid membrane channels formed by designed DNA nanostructures. Science. Nov. 16, 2012;338(6109):932-6. doi: 10.1126/science.1225624.

Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010. Author Manuscript, 21 pages.

Lu et al., Oxford Nanopore MinION Sequencing and Genome Assembly. Genomics Proteomics Bioinformatics. Oct. 2016;14(5):265-279. doi: 10.1016/j.gpb.2016.05.004. Epub Sep. 17, 2016.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

GB1808556.3, Feb. 6, 2019, Search Report.

PCT/GB2019/051441, Aug. 5, 2019, International Search Report and Written Opinion.

PCT/GB2019/051441, Dec. 3, 2020, International Preliminary Report on Patentability.

* cited by examiner

1.

2.

3.

6.

5.

4.

1    2    3    4    5    6    7    8    9

METHOD FOR SELECTING POLYNUCLEOTIDES BASED ON THE SIZE IN A GLOBULAR FORM

RELATED APPLICATIONS

This application is a national stage filing under 35 U.S.C. § 371 of international application number PCT/GB2019/051441, filed May 24, 2019, which claims the benefit of Great Britain application number GB 1808556.3, filed May 24, 2018, the entire contents of each of which is incorporated by reference.

FIELD OF THE INVENTION

The invention relates generally to methods of selecting polynucleotides. The invention also relates generally to methods of characterising a polynucleotide, and to kits for selecting polynucleotides. The methods are particularly suited to selecting polynucleotides for sequencing applications, such as nanopore sequencing.

BACKGROUND

Selection of polynucleotides based on size is important for many applications, such as sequencing DNA and RNA. There is a need for rapid and cheap polynucleotide characterisation, identification, amplification and sequencing technologies across a wide range of applications. The length of the polynucleotide can aid in the identification of the polynucleotide. The length and integrity of the polynucleotide can also affect the success and rapidity of downstream identification, amplification or sequencing applications. Many high-throughput DNA sequencers require insert libraries of certain sizes for optimum performance. Other examples of applications for which polynucleotide size selection is important include ensuring correct PCR product formation, genotyping, DNA fingerprinting, gene profiling, and extracting a fragment of a defined size, for example following enzymatic digestion of a polynucleotide.

DNA of different sizes is conventionally detected by gel electrophoresis. Manual gel electrophoresis methods have many drawbacks. For example, the equipment needed to achieve high-throughput separation on a commercially useful scale may be expensive and/or complex; the processing steps needed to allow the DNA to be processed using gel electrophoresis may risk contamination or degradation of the DNA sample; and/or the processes may involve the use of hazardous chemicals such as ethidium bromide, which is conventionally used to stain DNA. Automated electrophoresis instruments that separate and select DNA of desired size ranges between 100 bp and 50 kb have been developed, but these are complex and expensive.

Functionalised, paramagnetic silica particles under different reaction conditions may be used for DNA size selection. Typically, these methods only allow the separation of DNA<1 kb in length. Size exclusion methods using a solid matrix can also be used, but again, these are typically for the removal of short<1 kb DNA fragments from 1000 kb+fragments. These methods are thus typically unsuitable for the processing of longer DNA samples.

One key problem that is common to conventional techniques for selecting large DNA molecules on the basis of their size is that large DNA molecules are prone to shear during handling. The shear arises due to stresses during flow in solution, and increases in miniaturized systems. Shearing of DNA represents a serious problem when handling large DNA molecules.

There is thus a need for simple and effective methods for separation of DNA molecules of different sizes. There is particularly a need for methods of separating DNA molecules whilst avoiding or mitigating the effects of shear. The methods provided herein address this need, and are intended to address some or all of the above problems associated with conventional separation techniques.

SUMMARY

The inventors have devised a simple and effective method of selecting polynucleotides from a sample comprising a mixture of polynucleotides. The inventors have found that polynucleotides in the globular form can be readily size-selected in a robust and reproducible manner. The inventors have therefore developed methods for selecting polynucleotides based on the size of the polynucleotides in the globular form. The methods provided herein may be used to select polynucleotides of a desired length. The methods developed by the inventors are very different to conventional size-selection techniques (for example those set out above), which typically rely on the polynucleotides being in a non-globular form. Surprisingly, the inventors have further found that, by selecting polynucleotides in the globular form, the quality of characterisation data (e.g. sequencing data) that can be obtained from the size-selected sample is improved relative to data obtained on samples which have not been size-selected. Without being bound by theory, the inventors believe that such benefits may arise at least in part by avoiding shear and by thus obtaining high-quality homogeneous polynucleotide samples.

Accordingly, provided herein is a method for selecting polynucleotides, said method comprising:

i) providing a sample comprising a mixture of polynucleotides; and ii) selecting polynucleotides based on the size of the polynucleotides in a globular form.

Preferably, the method further comprises initially processing the sample such that the polynucleotides in the sample adopt a globular form and/or, after the selection step (ii), preferably processing the selected polynucleotides such that the selected polynucleotides adopt a non-globular form. Preferably, selecting the polynucleotides comprises filtering the sample through a filter. The sample may, for example:

a) comprise the products of a PCR reaction; and/or b) comprise a DNA library; and/or c) comprise genomic DNA; and/or d) comprise the products of an endonuclease digestion.

Also provided is a method of characterising a polynucleotide, the method comprising:

i) carrying out a method for selecting polynucleotides as described herein;

ii) contacting a transmembrane pore with the selected polynucleotides;

iii) applying a potential difference across the transmembrane pore; and iv) taking one or more measurements which are indicative of one or more characteristics of a polynucleotide moving with respect to the transmembrane pore and thereby characterising the polynucleotide.

Further provided is a kit for separating polynucleotides, the kit comprising a filter, a condensing medium as described herein and optionally further comprising an extending medium as described herein.

DESCRIPTION OF THE FIGURES

It is to be understood that Figures are for the illustration purposes and are not intended to be limiting.

In FIG. 1, the polynucleotides in the sample are initially in a non-globular (linear) form (panel 1). In the methods provided herein, the polynucleotides in the sample may alternatively be initially in globular form. The polynucleotides in the sample may be processed for example by contacting the polynucleotides with a condensing medium such that the polynucleotides in the sample adopt a globular form (panel 2). Polynucleotides in the globular form may then be selected, for example by contacting of the polynucleotides with a filter represented by the dashed line (panel 3) and passing of unselected polynucleotides through the filter such that the selected polynucleotides are retained by the filter (panel 4). For avoidance of doubt, and as described in more detail herein, other selecting means and other configurations of selecting polynucleotides are also in accordance with the methods provided herein. For example, the methods provided herein also provide selection of polynucleotides from the sample such that selected polynucleotides pass through the filter and the unselected polynucleotides are retained by the filter. The thus selected polynucleotides may be isolated in globular form if required (panel 5). The selected polynucleotides may optionally be processed such that the selected polynucleotides adopt a non-globular form (panel 6).

4

DETAILED DESCRIPTION

Figure 1:
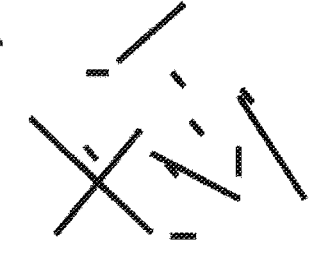
FIG. 1 shows a schematic representation of size-selecting polynucleotides in accordance with the methods provided herein. Step 1 shows a polynucleotide sample comprising a mixture of polynucleotides.
Figure 1:
Figure 1:
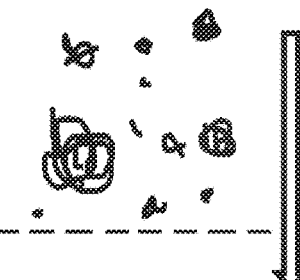
Figure 1:
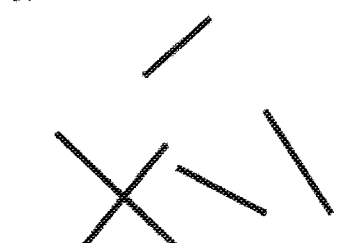
Figure 1:
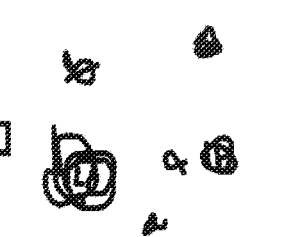
Figure 1:
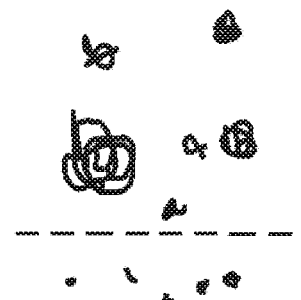

It is to be understood that different applications of the disclosed methods and products may be tailored to the specific needs in the art. It is also to be understood that the terminology used herein is for the purpose of describing particular embodiments of the methods and products only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "a transmembrane pore" includes two or more pores, etc.

All publications, patents and patent applications cited herein, whether supra or infra, are hereby incorporated by reference in their entirety.

General Method

The inventors have devised a method for selecting polynucleotides, the method comprising:

i) providing a sample comprising a mixture of polynucleotides; and ii) selecting polynucleotides based on the size of the polynucleotides in a globular form.

Globular and Non-Globular Forms

Polynucleotides can exist in multiple forms. Polynucleotides can exist in globular or non-globular forms. Non-globular forms are also referred to as liner forms, coiled forms, relaxed forms and/or extended forms. Globular forms are also referred to as condensed forms, compressed forms and/or close-packed forms. As those skilled in the art will appreciate, polynucleotides in non-globular forms are extended relative to when in globular forms. Globular polynucleotides are highly condensed relative to non-globular polynucleotides. The polynucleotides in globular forms may for example adopt a close-packed structure, e.g. strands of polynucleotides may arrange in a hexagonal close packed arrangement. Alternatively, the globular form may be less rigidly ordered. Beneficially, polynucleotides in the globular form are resilient to precipitation and/or aggregation and can be handled in a relatively robust manner.

When in a globular form the size of a given polynucleotide will depend on the length of that polynucleotide in a non-globular form. It has been shown that DNA molecules in the globular form for example as induced by PEG can be manipulated. For example, capillaries have been used to perform manipulations of globular polynucleotides that are difficult to achieve using non-globular polynucleotides. However, the selection of polynucleotides based on the size of the polynucleotides in a globular form has not previously been achieved. The inventors have now recognised that one or more polynucleotides of a desired size in the non-globular form can be selected from a mixture comprising such polynucleotides and polynucleotides having a non-desired size by selecting polynucleotides having a desired size in a globular form, and have developed the methods provided herein in order to select polynucleotides in this manner.

The inventors have recognised that large polynucleotides are prone to shear during handling. As explained above, the shear arises due to stresses during flow in solution, and increases in miniaturized systems. Shearing represents a serious problem when handling large polynucleotide molecules. Shearing is a particular problem encountered when size-selecting polynucleotides using conventional techniques, not least as such techniques often involve pipetting samples containing the polynucleotides to be selected. Pipettes used for such pipetting typically have a very small aperture and induce large shear forces on the polynucleotides thus manipulated, thereby leading to fracturing. The methods provided herein are intended to address this issue. The inventors have further recognised that shearing is suppressed when the polynucleotides are in the globular form. Preferably, therefore, the methods provided herein involve selecting polynucleotides in the globular form wherein the globular form is a condensed form wherein the polynucleotides are resistant to shear.

Selecting

The selection method is used to distinguish polynucleotides having different sizes in the globular form. A number of different selections could be performed in combination. In one embodiment, the method selects polynucleotides that can then be separated and/or selectively modified based on their lengths. Preferably, the method is used to select long polynucleotides. The length of the selected polynucleotides may vary depending on what is desired. The method may be adjusted such that polynucleotides of the desirable length are selected. For example, the method may be used to select polynucleotides having a length of at least 1 kb, e.g. at least 10 kb, such as at least 50 kb, for example at least 100 kb, e.g. at least 1,000 kb, such as at least 10,000 kb, e.g. at least 100,000 kb, such as at least 200,000 kb, for example at least 250,000 kb.

The method may be used to select polynucleotides that fall within a particular "window". For example, the method may be carried out two or more times to select a polynucleotide within a defined range of lengths, i.e. by removing polynucleotides that are shorter than the desired length and then polynucleotides that are longer than the desired length or vice versa.

Initial Processing

In step (i) of the method, the polynucleotides in the sample may initially be a non-globular form, e.g. an extended form. Alternatively, the polynucleotides in the sample may initially be in a globular form. Preferably, in the method, in step (i) of the method, the polynucleotides in the sample are initially in an extended form. When the polynucleotides in the sample are initially in a non-globular form, step (i) of the method may further comprise processing the sample such that the polynucleotides in the sample adopt a globular form.

Polynucleotides can be transformed from non-globular forms to globular forms by any appropriate processing step. Preferably, in the method, polynucleotides in a non-globular form may be contacted with a condensing medium so as to adopt a globular form. Suitable condensing media are described further herein. The transition of polynucleotides from the non-globular form to the globular form can be described as a φ transition as it can be induced by polymers and salts.

Further Processing

After selecting polynucleotides based on the size of the polynucleotides in a globular form in step (ii) of the method, the selected polynucleotides are initially in a globular form following their selection. For some applications it is preferable to retain selected polynucleotides in a globular form. This can be preferable, for example if further manipulations of the selected polynucleotides are required and such manipulations render the selected polynucleotides susceptible to shear. For other applications it is preferable that the selected polynucleotides are in a non-globular form. This can be preferable for example for characterising the selected polynucleotides. Exemplary characterisation steps that can be performed on the selected polynucleotides are described in more detail herein.

For applications where it is desired that the selected polynucleotides are in a non-globular form, it is thus necessary to process the selected polynucleotides. Accordingly, the method may preferably further comprise:

iii) processing the selected polynucleotides such that the selected polynucleotides adopt a non-globular form.

Polynucleotides can be transformed from globular forms to non-globular forms by any appropriate processing step. Preferably, in the method, selected polynucleotides in a globular form may be contacted with an extending medium so as to adopt a non-globular form. Suitable extending media are described further herein.

The length of the selected polynucleotides may vary depending on what is desired. Accordingly, in the method, the selected polynucleotides are preferably longer or shorter than the unselected polynucleotides. More preferably the selected polynucleotides are longer than the unselected polynucleotides. For example, the selected polynucleotides may preferably have a length of at least 1 kb, 10 kb, 50 kb, 100 kb, 1,000 kb, or 10,000 kb, and the unselected polynucleotides may preferably have a length of at most 10,000 kb, 1,000 kb, 100 kb, 50 kb, 10 kb or 1 kb.

Filter

The methods provided herein may comprise selecting polynucleotides by filtering the sample through a filter.

The methods may comprise selecting polynucleotides by passing the sample through a filter such that the selected polynucleotides are retained by the filter and the unselected polynucleotides pass through the filter. Such methods may be particularly suitable for selecting large polynucleotides from a sample comprising both large polynucleotides and smaller polynucleotides.

Alternatively, the methods may comprise selecting polynucleotides by passing the sample through a filter such that the selected polynucleotides pass through the filter and the unselected polynucleotides are retained by the filter. Such methods may be particularly suitable for selecting small polynucleotides from a sample comprising both small polynucleotides and larger polynucleotides.

In a further alternative, selecting polynucleotides may involve retaining selected polynucleotides by the filter and further retaining selected polynucleotides that pass through the filter. Such methods may be particularly suitable when a sample comprises both small polynucleotides and larger polynucleotides and it is desired to separately select both the small polynucleotides and the larger polynucleotides.

In the methods provided herein, a filter is typically used to select polynucleotides from the sample. A filter is typically a semi-permeable medium, and is typically porous. Fluids can pass through the pores of the filter whilst solids are retained based on their size relative to the size of the pores in the filter. Particles smaller than the pore size of the filter may pass through the filter whereas particles larger than the pore size of the filter are retained by the filter. Preferably, in the methods, polynucleotides retained by the filter may be dried e.g. by drying the filter by contacting the filter with a stream of air or other gas. Any gas may be used. Preferred gases include air, nitrogen, argon, etc.

In the methods, any suitable filter can be used. Those skilled in the art will be readily able to select appropriate filters in accordance with the properties of the sample and the polynucleotides to be selected.

A filter to be used in the methods can be selected based on its pore size. Those skilled in the art will be able select appropriate pore sizes in accordance with the properties of the sample and the polynucleotides to be selected. Preferably, the pore size of the filter may be from about 0.01 μm to about 100 μm; e.g. from about 0.01 μm to about 25 μm; such as from about 0.01 μm to about 5 μm; more preferably from about 0.1 μm to about 1 μm e.g. from about 0.2 μm to about 0.6 μm for example from about 0.4 to about 0.5 μm. Filters having appropriate sizes for use in accordance with the methods are commercially available from suppliers such as Corning (US) and are, for example, available with pore sizes including 0.1 μm, 0.2 μm, 0.45 μm; 5 μm and the like.

The filter can be for example a membrane filter. A membrane filter can be used in any suitable configuration. For example, a membrane filter can be used as a "bottle top" filter or a syringe filter. Syringe filters are preferred in the methods provided herein. Syringe filters are commercially available e.g. from Corning (US) or can be specifically fabricated for the intended application. Preferably, the syringe filter has a dead volume of less than 100 μL, more preferably less than 50 μL e.g. less than 20 μM more preferably less than 10 μL.

Syringes suitable for use in the methods provided herein (e.g. when the filter is a syringe filter) include syringes having volumes of from about 0.1 mL to about 25 mL or about 50 mL, such as from about 0.1 to about 5 mL or 10 mL, preferably from about 1 mL to about 2 mL. Any suitable syringe material can be used. Preferred syringe housing materials include those which resist adsorption by the poly-nucleotides in the sample. Preferred syringe housing materials include glass and polymeric materials. Preferred polymeric materials for use as the syringe housing include polystyrene (PS), acrylic copolymer (AC), polyvinyl chloride (PVC) and polypropylene (PP).

Membrane filters can be made of any suitable material. Preferred materials include polymers. The filter may preferably be made of a polysaccharide (including modified polysaccharides) or a synthetic polymer. Preferably, the filter material comprises or consists of cellulose nitrate, cellulose acetate, nylon, polyethersulfone, regenerated cellulose and/or polytetrafluoroethylene. More preferably, the filter material comprises or consists of nylon, cellulose acetate, polyethersulfone, or regenerated cellulose, still more preferably the filter material comprises or consists of cellulose acetate, polyethersulfone, or regenerated cellulose.

Condensing Medium

As explained above, polynucleotides can be transformed from non-globular forms to globular forms by any appropriate processing step. Preferably, in the methods provided herein, polynucleotides in a non-globular form may be contacted with a condensing medium so as to adopt a globular form. Accordingly, in the methods, step (i) preferably comprises processing the sample such that the poly-nucleotides in the sample adopt a globular form, wherein said processing comprises contacting the sample with a condensing medium.

Selecting polynucleotides in accordance with the methods provided herein involves selecting polynucleotides in the globular state. Those skilled in the art will appreciate that globular states do not include precipitated forms of the polynucleotides. Precipitation of polynucleotides such as DNA can occur due to ionic interactions between the charged phosphate backbone of the polynucleotide and positively charged cations in solution. Decreasing the ability of such charges to be screened, e.g. by adding a solvent to the polynucleotides in solution wherein the added solvent is less polar than the solvent comprised in the solution can thus prevent adequate charge screening causing the polynucle-otide to precipitate out of solution. Accordingly, when the methods comprise processing the sample by contacting the sample with a condensing medium, such that the polynucleotides in the sample adopt a globular form, it is preferable to use condensing mediums that do not promote precipitation.

A condensing medium is a medium which promotes the formation of the globular state by polynucleotides which are in a non-globular state. Any suitable condensing medium can be used in the methods provided herein. Preferably, the condensing medium is a salt solution comprising a hydrophilic polymer. The condensing medium does not cause the polynucleotides in the sample to precipitate.

In preferred condensing mediums for use in the methods provided herein, the hydrophilic polymer is a polyether or a polysaccharide. Preferably, the hydrophilic polymer is a polyether. Preferred polyethers for use in condensing media for use in accordance with the methods are polyethylene glycol (PEG) and modified polyethylene glycols. Preferred polysaccharides for use in condensing media for use in accordance with the methods include dextran and modified dextrans (e.g. dextran sulphate). Modified and unmodified polyethylene glycols and dextrans are commercially available, e.g. from Sigma Aldrich. When the polyether is poly-ethylene glycol, any suitable polyethylene glycol can be used. Preferably, the polyethylene glycol has a molecular weight of from about 2000 Da to about 12000 Da; more preferably from about 4000 Da to about 10000 Da e.g. from about 6000 Da to about 8000 Da. PEG having a molecular weight of about 6000 Da is also referred to as PEG 6K; PEG having a molecular weight of about 8000 Da is also referred to as PEG 8K; etc.

In preferred condensing mediums for use in the methods provided herein, the salt solution preferably comprises a group (I) or group (II) metal salt. Preferred metal salts are sodium salts, potassium salts, magnesium salts and calcium salts. Sodium and potassium salts are preferred, preferably sodium salts. Any suitable counterion (anion) can be used. Preferred anions include halide, nitrate, phosphate, carbonate, and organic anions such as acetate etc. Preferably the metal salt is a group (I) or group (II) metal halide, preferably a chloride. Most preferably the metal salt is sodium chloride or potassium chloride, preferably sodium chloride.

Accordingly, in preferred condensing mediums for use in the methods provided herein:

i) the hydrophilic polymer is a polyether or a polysac-charide, optionally wherein the hydrophilic polymer is polyethylene glycol having a molecular weight of from 2000 to 12000; and/or ii) the salt solution comprises a group (I) or group (II) metal salt, optionally wherein the metal salt is a metal halide.

In preferred condensing mediums for use in the methods provided herein, the hydrophilic polymer is present in a concentration of from about 10 to about 200 mg/mL; more preferably from about 20 to about 150 mg/mL e.g. from about 30 to about 100 mg/mL, for example from about 40 to about 80 mg/mL preferably from about 50 to about 70 mg/mL e.g. about 60 mg/mL.

In preferred condensing mediums for use in the methods provided herein, the salt concentration in the condensing medium is present in a concentration of from about 0.1 M to about 1 M; more preferably from about 0.3 to about 0.8 M for example from about 0.5 to about 0.7 M e.g. about 0.6 M.

Accordingly, in preferred condensing mediums for use in the methods provided herein i) the polymer concentration in the condensing medium is from about 10 to about 200 mg/mL; and/or ii) the salt concentration in the condensing medium is from about 0.1 to about 1 M.

Particularly preferred condensing mediums for use in the methods therefore comprise:

i) from about 40 mg/mL to about 80 mg/mL, preferably from about 50 mg/mL to about 70 mg/mL of polyethylene glycol having a molecular weight of from about 4000 Da to about 10000 Da, preferably from about 6000 Da to about 8000 Da; and ii) from about 0.3 M to about 0.8 M, preferably from about 0.5 M to about 0.7 M of a group (I) or group (II) metal halide, preferably sodium chloride.

Most preferably the condensing medium is or comprises about 60 mg/mL PEG 6K and about 0.6 M sodium chloride.

Extending Medium

As explained above, polynucleotides can be transformed from globular forms to non-globular forms by any appropriate processing step. Preferably, in the methods provided herein, polynucleotides in a globular form may be contacted with an extending medium so as to adopt a non-globular form. Accordingly, the methods preferably further comprise:

iii) processing the selected polynucleotides such that the selected polynucleotides adopt a non-globular form.

In such methods, step (iii) preferably comprises processing the selected polynucleotides such that the selected polynucleotides adopt a non-globular form, wherein said processing comprises contacting the selected polynucleotides with an extending medium.

An extending medium is a medium which promotes the formation of the non-globular state by polynucleotides which are in a globular state. Any suitable extending medium can be used in the methods provided herein. Preferably, the extending medium is an aqueous solution that does not comprise high concentrations of a hydrophilic polymer. Preferably, the extending medium is an aqueous solution that does not comprise high concentrations of a salt. In embodiments which comprise the use of both a condensing medium as defined herein and an extending medium as defined herein, preferably the concentration of salt in the extending medium is lower than the concentration of salt in the condensing medium. In embodiments which comprise the use of both a condensing medium as defined herein and an extending medium as defined herein, preferably the concentration of hydrophilic polymer in the extending medium is lower than the concentration of hydrophilic polymer in the condensing medium. Preferably the extending medium is or comprises a buffer solution.

Preferred extending mediums for use in the methods provided herein thus comprise an aqueous solution which is free or substantially free of hydrophilic polymers. Preferably, the aqueous solution is free of enzymes that can degrade polynucleotides such as DNase and RNase. The aqueous solution can optionally be water. Preferably, the aqueous solution is an aqueous buffer solution. Any suitable buffers can be used. Preferably the buffer is an organic buffer such as Tris (tris(hydroxymethyl)aminomethane). Preferably, the buffer comprises an agent for chelating metals. Suitable agents include EDTA, citric acid and borate. EDTA is preferred. Preferably the buffer comprises Tris and EDTA. Preferably the Tris is present in a concentration of from about 1 mM to about 50 mM e.g. from about 10 mM to about 20 mM, and/or preferably the EDTA is present in an amount of from about 0.1 mM to about 5 mM e.g. from about 1 mM to about 2 mM. Preferably the buffer has a pH of from about 6 to about 9, e.g. from about 7 to about 8.

Accordingly, preferred extending mediums for use in the methods provided herein:

i) comprise from about 1 mM to about 50 mM, preferably from about 10 mM to about 20 mM, of an organic buffer, preferably Tris;

ii) comprise from about 0.1 mM to about 5 mM, preferably from about 1 mM to about 2 mM, of a chelating agent, preferably EDTA; and iii) have a pH of from about 6 to about 9.

Most preferably the extending medium is or comprises TE buffer (about 10 mM TRIS; about 1 mM EDTA; having a pH of about 8).

When the methods comprise the selection of polynucleotides using a filter, the selected polynucleotides may be free of the filter once selected. Alternatively the selected polynucleotides may partially or wholly bind to the filter. Accordingly, in methods which comprise selecting polynucleotides by filtering the sample through a filter and also comprise processing the selected polynucleotides such that the selected polynucleotides adopt a non-globular form by contacting the selected polynucleotides with an extending medium, preferably the extending medium is used to elute the selected polynucleotides from the filter. Eluting the selected polynucleotides from the filter can be achieved by washing the filter with the extending medium. When the filter is a syringe filter, the syringe can be used to pump or draw eluting medium through the syringe filter. Such methods can be beneficial as processing the selected polynucleotides such that the selected polynucleotides adopt a non-globular form and eluting the selected polynucleotides from the filter can be achieved simultaneously which can offer advantages of processing simplicity, improved speed and reduced scope for contamination of the selected polynucleotides.

Sample

The sample comprises a mixture of polynucleotides. The sample may be any suitable sample comprising polynucleotides. The polynucleotides may, for example, comprise the products of a PCR reaction, genomic DNA, the products of an endonuclease digestion and/or a DNA library.

The sample may be a biological sample. The method may be carried out in vitro on a sample obtained from or extracted from any organism or microorganism. The organism or microorganism is typically archaean, prokaryotic or eukaryotic and typically belongs to one of the five kingdoms: plantae, animalia, fungi, monera and protista. The method may be carried out in vitro on a sample obtained from or extracted from any virus.

The sample is preferably a fluid sample. The sample typically comprises a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs.

Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to carrying out the method, for example by centrifugation or by passage through a membrane that filters out unwanted molecules or cells, such as red blood cells. The method may be performed on the sample immediately upon being taken. The sample may also be typically stored prior to the method, preferably below −70° C.

The sample may comprise genomic DNA. The genomic DNA may be fragmented. The DNA may be fragmented by any suitable method. For example, methods of fragmenting DNA are known in the art, Such methods may use a transposase, such as a MuA transposase. Preferably the genomic DNA is not fragmented.

The polynucleotides separated by the method may be, for example, DNA, RNA and/or DNA/RNA hybrids. The DNA may be double stranded or single stranded. The sample may comprise DNA and the selected and unselected polynucleotides may each comprise DNA. Alternatively, the sample may comprise RNA and the selected and unselected polynucleotides may each comprise RNA. In a further alternative, the sample may comprise DNA and RNA and the selected polynucleotides may comprise DNA and unselected polynucleotides may comprise RNA; or the selected polynucleotides may comprise RNA and unselected polynucleotides may comprise DNA. Preferably the polynucleotides in the sample are double stranded DNA.

Accordingly, the method may be used to separate a desired sub-population of target polynucleotides from a population comprising both the sub-population of target polynucleotides and polynucleotides of length greater and/or less than the desired sub-population. For example, the method may be used to separate a sub-population of shorter polynucleotides (e.g. DNA, such as double-stranded DNA) from a population comprising the sub-population of shorter polynucleotides and a sub-population of longer polynucleotides (e.g. longer DNA, such as double-stranded DNA). The method may be used to separate a sub-population of longer polynucleotides (e.g. DNA, such as double-stranded DNA) from a population comprising the sub-population of longer polynucleotides and a sub-population of shorter polynucleotides (e.g. longer DNA, such as double-stranded DNA). The methods typically do not comprise precipitation of the polynucleotides. The methods typically comprise filtering the sample through a filter.

In other words, the method may be used to select polynucleotides (e.g. DNA, such as double-stranded DNA) having lengths lower than a threshold value from a sample comprising polynucleotides having lengths greater than the threshold value. The method may be used to select polynucleotides (e.g. DNA, such as double-stranded DNA) having lengths greater than a threshold value from a sample comprising polynucleotides having lengths lower than the threshold value. The threshold value in such methods may be for example approximately 1 kb, 2 kb, 5 kb, 10 kb, 15 kb, 20 kb, 25 kb, 50 kb, 100 kb, etc. As such, the method may be used to select polynucleotides (e.g. DNA, such as double-stranded DNA) having lengths lower than 1 kb, 2 kb, 5 kb, 10 kb, 15 kb, 20 kb, 25 kb, 50 kb, or 100 kb etc from a wider population of polynucleotides. The method may be used to select polynucleotides (e.g. DNA, such as double-stranded DNA) having lengths greater than 1 kb, 2 kb, 5 kb, 10 kb, 15 kb, 20 kb, 25 kb, 50 kb, or 100 kb etc from a wider population of polynucleotides. The methods typically do not comprise precipitation of the polynucleotides. The methods typically comprise filtering the sample through a filter.

Modifications to Selected Polynucleotides

The selected polynucleotides in the sample may be modified or unmodified. The selected polynucleotides in the sample may be modified before their selection and subsequently selected or they may be initially unmodified and then modified post selection. Any suitable modification can be made. For example, one or more sequencing adapters may be added to one or both ends of the polynucleotides in the sample. For example the adapters may be designed for single or double-ended attachment. Suitable adapters are defined below.

Sequencing Adapter

An adapter may be attached to one or both ends of the selected polynucleotides. As described in more detail below, a nucleic acid handling enzyme may optionally be pre-bound to the adapter. The nucleic acid handling enzyme may be pre-bound to one or both ends of each of the selected polynucleotides under conditions where the enzyme does not move along the polynucleotides. The enzyme may be stalled on the adapter. The enzyme may be stalled by virtue of the absence of fuel and/or a necessary cofactor. The enzyme may be stalled in the presence of fuel, using a stall that can be removed/overcome to initiate movement of the enzyme (e.g. by toehold displacement).

The same adapter may be added to both ends of the selected polynucleotides. Alternatively, different adapters may be added to the two ends of each of the selected polynucleotides. An adapter may be added to just one end of each of the selected polynucleotides. Methods of adding adapters to polynucleotides are known in the art. Adapters may be attached to polynucleotides, for example, by ligation, by click chemistry, by tagmentation, by topoisomerisation or by any other suitable method.

The adapter is preferably capable of being attached to the end of a polynucleotide to which a nucleic acid handling enzyme can bind. The adapter is preferably synthetic or artificial. The adapter preferably comprises a polymer. The polymer is preferably a polynucleotide. The polynucleotide adapter may comprise DNA, RNA, modified DNA (such as a basic DNA), RNA, PNA, LNA, BNA and/or PEG. The adapter more preferably comprises single stranded and/or double stranded DNA or RNA.

The adapter may comprise a single stranded polynucleotide to which a nucleic acid handling enzyme may be bound.

In one embodiment, the adapter is a Y adapter. A Y adapter is typically a polynucleotide adapter. A Y adapter is typically double stranded and comprises (a) at one end, a region where the two strands are hybridised together and (b), at the other end, a region where the two strands are not complementary. The non-complementary parts of the strands form overhangs. The presence of a non-complementary region in the Y adapter gives the adapter its Y shape since the two strands typically do not hybridise to each other unlike the double stranded portion. A nucleic acid handling enzyme may be bound to an overhang and/or to the double stranded region. In one embodiment, a first nucleic acid handling enzyme may be bound to the double stranded region and a second nucleic acid handling enzyme may be is bound to an overhang. The second enzyme on the overhang is preferably stalled by a spacer. In one embodiment the Y adapter comprises a membrane anchor or a pore anchor as described in more detail herein. The anchor may be attached to a polynucleotide that is complementary to and hence that is hybridised to the overhang to which an nucleic acid handling enzyme is bound.

One of the non-complementary strands of a Y adapter may comprise a leader sequence, which when contacted with a transmembrane pore is capable of threading into the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader sequence preferably comprises a polynucleotide and more preferably comprises a single stranded polynucleotide. The single stranded leader sequence most preferably comprises a single strand of DNA, such as a poly dT section. The leader sequence preferably comprises the one or more spacers. The leader sequence can be any length, but is typically 10 to 150 nucleotides in length, such as from 20 to 120, 30 to 100, 40 to 80 or 50 to 70 nucleotides in length.

The adapter may be a hairpin loop adapter. A hairpin loop adapter is an adapter comprising a single polynucleotide strand, wherein the ends of the polynucleotide strand are capable of hybridising to each other, or are hybridized to each other, and wherein the middle section of the polynucleotide forms a loop. Suitable hairpin loop adapters can be designed using methods known in the art. The loop may be any length. The loop is preferably from about 2 to 400, from 5 to 300, from 10 to 200, from 20 to 100 nucleotides or from 30 to 50 in length. The double stranded section of the adapter formed by two hybridized sections of the polynucleotide strand is called a stem. The stem of the hairpin loop is preferably from 4 to 200, such as 5 to 150, 10 to 100, 20 to 90, 30 to 80, 40 to 70 or 50 to 60 nucleotide pairs in length. If a nucleic acid handling enzyme is bound to or binds to a hairpin adapter, it typically binds to the loop of the hairpin, rather than to the stem.

If the selected polynucleotides are double stranded, a Y adapter may be added to one end and a hairpin loop adapter to the other end. In this embodiment, a nucleic acid handling enzyme may be bound to the Y adapter and/or to the hairpin adapter.

An adapter may be attached to the selected polynucleotides in any manner. The adapters are preferably covalently attached to the selected polynucleotides. The adapters may be ligated to the selected polynucleotides. The adapters may be ligated to either end of the polynucleotide, i.e. the 5' or the 3' end, or to both ends of the polynucleotide i.e. to the 5' end and to the 3' end. The adapters may be ligated to the polynucleotide using any method known in the art. The adapter may be ligated to the polynucleotides in the absence of ATP or using gamma-S-ATP (ATPγS) instead of ATP. It is preferred that the adapter is ligated to the polynucleotides in the absence of ATP where the nucleic acid handling enzyme is bound to the adapter. The adapter may be ligated using a ligase, such as T4 DNA ligase, E. coli DNA ligase, Taq DNA ligase, Tma DNA ligase and 9° N DNA ligase. The ligase may be removed from the sample before step (i) of the method. The adapter may be attached using a topoisomerisase. The topoisomerase may, for example be a member of any of the Moiety Classification (EC) groups 5.99.1.2 and 5.99.1.3.

An adapter which may be used in accordance with the methods provided herein may have bound thereto a nucleic acid handling enzyme which is bound such that its movement along the adapter is hindered or prevented until it is brought into contact with a transmembrane pore under an applied potential. In this embodiment, the adapter preferably comprises a polynucleotide and/or the nucleic acid handling enzyme is preferably a translocase or helicase. Movement of the nucleic acid handling enzyme may be hindered or prevented by being stalled at a spacer, for example as disclosed in WO 2014/135838. Any configuration of enzymes and spacers disclosed in WO 2014/135838 may be used in the method of separating polynucleotides.

The spacer is preferably part of the adapter, for instance the spacer may interrupt the polynucleotide sequence in the adapter. There may be any number of spacers in the adapter, such as 1, 2, 3, 4, 5, 6, 7, 8, 9, 10 or more spacers. There are preferably one, two, four or six spacers in the target polynucleotide. The nucleic acid handling enzyme is preferably on the side of the spacer that is towards the end of the adapter that is attached to, or is for attachment to, a polynucleotide. Alternatively, the nucleic acid handling enzyme may be on the side of the spacer that is away from the end of the adapter that is attached to, or is for attachment to, a polynucleotide. Alternatively, the second enzyme may be positioned on the spacer.

The spacer provides an energy barrier which the enzyme cannot overcome even in the presence of fuel and the necessary coenzymes and/or cofactors. The spacer may stall the enzyme by reducing the traction of the enzyme (for example the bases from the nucleotides in the spacer may be missing) or by physically blocking movement of the one or more helicases (for example, the spacer may comprise a bulky chemical group).

The spacer may comprise any molecule or combination of molecules that hinders or prevents the enzyme from moving along the target polynucleotide. It is straightforward to determine whether or not an enzyme is stalled at a spacer, in the absence of a transmembrane pore and an applied potential. For example, the ability of an enzyme to move past a spacer and displace a complementary strand of DNA can be measured by polyacrylamide gel electrophoresis (PAGE).

The spacer typically comprises a linear molecule, such as a polymer. The spacer typically has a different structure from the target polynucleotide. For instance, if the target polynucleotide is DNA, the one or more spacers are typically not DNA. In particular, if the target polynucleotide is deoxyribonucleic acid (DNA) or ribonucleic acid (RNA), the spacer preferably comprise peptide nucleic acid (PNA), glycerol nucleic acid (GNA), threose nucleic acid (TNA), locked nucleic acid (LNA) or a synthetic polymer with nucleotide side chains. The spacer may comprise one or more nucleotides in the opposite direction from other nucleotides in the adapter. For example, the spacer may comprise one or more nucleotides in the 3' or 5' direction when the polynucleotide is in the 5' to 3' direction.

The spacer preferably comprises one or more nitroindoles, such as 5-nitroindoles, inosines, acridines, 2-aminopurines, 2-6-diaminopurines, 5-bromo-deoxyuridines, inverted thymidines (inverted dTs), inverted dideoxy-thymidines (ddTs), dideoxy-cytidines (ddCs), 5-methylcytidines, 5-hydroxymethylcytidines, 2'-O-Methyl RNA bases, Iso-deoxycytidines (Iso-dCs), Iso-deoxyguanosines (Iso-dGs), iSpC3 groups (i.e. nucleotides which lack sugar and a base), photo-cleavable (PC) groups, hexandiol groups, spacer 9 (iSp9) groups, spacer 18 (iSp18) groups, a polymer or thiol connections. The spacers may comprise any combination of these groups. Many of these groups are commercially available from IDT® (Integrated DNA Technologies®).

The spacer may contain, for example, 2, 3, 4, 5, 6, 7, 8, 9, 10, 11, 12 or more 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, 2, 3, 4, 5, 6, 7, 8, 9, 10, 11, 12 or more. The spacer preferably comprises 2, 3, 4, 5, 6, 7, 8 or more iSp9 groups and/or 2, 3, 4, 5 or 6 or more iSp18 groups. The most preferred spacer is four iSp18 groups.

Where the spacer comprises a polymer, the polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The spacer may comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into target polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The nucleic acid handling enzyme may be stalled before or on a linear molecule spacer. If a linear molecule spacer is used, the adapter preferably comprises a double stranded region of polynucleotide adjacent to the end of the spacer closest to the end of the adapter which is attached to, or is for attachment to, the polynucleotide. A hybridized double stranded region preferably terminates at the spacer and the strand that does not comprise the spacer preferably forms an overhang adjacent to the spacer. A further polynucleotide strand may be hybridized to the overhang to form a further double stranded region. The further double stranded region typically helps to stall the second enzyme on the spacer. The further polynucleotide is typically formed from the same nucleotides as the target polynucleotide, but may be formed from different nucleotides. For instance, the further polynucleotide may be formed from locked nucleic acid (LNA) or bridged nucleic acid (BNA).

If a linear molecule spacer is used, the adapter preferably comprises a blocking molecule at the end of the spacer. The blocking molecule may help to ensure that the second enzyme remains stalled on the spacer. The blocking molecule may be any chemical group which physically causes the one or more helicases to stall. The blocking molecule may be a double stranded region of polynucleotide.

Suitable chemical groups include pendant chemical groups. The chemical group may be attached to one or more nucleobases in the target polynucleotide and/or to the polynucleotide backbone. Any number of chemical groups may be present, such as 1, 2, 3, 4, 5, 6, 7, 8, 9, 10, 11, 12 or more. Examples of suitable groups include, but are not limited to, fluorophores, streptavidin and/or biotin, cholesterol, methylene blue, dinitrophenols (DNPs), digoxigenin and/or antidigoxigenin and dibenzylcyclooctyne groups.

Where more than one spacer is present in an adapter they may be the same or different. For example, one spacer may comprise one of the linear molecules discussed above and another spacer may comprise one or more chemical groups which physically stall the second enzyme. A spacer may comprise any of the linear molecules discussed above and one or more chemical groups, such as one or more abasics and a fluorophore.

Most nucleic acid handling enzymes, such as helicases, bind and move along DNA and so may be stalled using anything that is not DNA.

In the absence of a transmembrane pore and an applied potential, the spacer is preferably capable of stalling the nucleic acid handling enzyme in the presence of free nucleotides and/or the presence of a cofactor. The ability of a spacer to stall an enzyme may be affected by salt concentration. The higher the salt concentration used, the shorter the one or more spacers need to be. In the absence of a transmembrane pore and an applied potential, the spacer is preferably capable of stalling the nucleic acid handling enzyme at a salt concentration of less than about 100 mM.

Examples of spacers that can be used to stall an enzyme that processes DNA in the presence of free nucleotides and a cofactor include: at 1M salt, 4 iSpC3 groups or 2 iSp18 groups; at 100-1000 mM salt, 4 iSp18 groups or 6 iSp9 groups; at <100-1000 mM salt, 6 iSp18 groups, 12 iSpC3 groups or 20 iSpC3 groups. The enzyme can be 'pushed over' a stalling chemistry by annealing a DNA strand behind the enzyme, e.g. by toehold displacement. Alternatively, the enzyme can be 'stalled' using a condition in which it is unable to translocate. For example, the adapter may be kept in a pH at which the enzyme is unable to translocate and/or bind fuel. A small molecule inhibitor could alternatively be used to stall an enzyme.

An adapter which may be attached to the selected polynucleotides may comprise a tag. The tag may be hybridized to the adapter or may be attached to the enzyme. Suitable tags are known in the art. Examples of suitable tags include, but are not limited to, biotin, a selectable polynucleotide sequence, antibodies, antibody fragments, such as Fab and ScSv, antigens, polynucleotide binding proteins, poly histidine tails and GST tags. Biotin specifically binds to a surface coated with avidins, such as streptavidin. Selectable polynucleotide sequences specifically bind (i.e. hybridise) to a surface coated with complementary sequences.

The adapter and/or the tag may comprise a region that can be cut, nicked, cleaved or hydrolysed. Suitable sites are known in the art. Suitable sites include, but are not limited to, an RNA region, a region comprising desthiobiotin and streptavidin, a disulphide bond, a photocleavable region and a restriction enzyme site, or other site that is selectively cleaved by an enzyme.

The adapter may, in addition to or instead of a tag, comprise a hidden site for attaching a further polynucleotide and/or other molecule, such as, for example, a protein. The adapter may, in addition to or instead of a tag, comprise an exposed site for attaching a further polynucleotide and/or other molecule, such as, for example, a protein. A site for attaching a further polynucleotide may, for example, be a single stranded region that is capable of hybridising to a complementary polynucleotide strand or to a strand comprising or consisting of universal bases, such as inosines. The complementary polynucleotide strand may be DNA, RNA, a DNA/RNA hybrid, PNA, LNA, BNA and/or. a strand comprising or consisting of modified bases. The modified bases may, for example, be abasic nucleotides, such as nucleotides in which the nucleobase is replaced by —H (idSp) or —OH. The modified bases may, for example, include one or more of 3-methyladenine, 7-methylguanine, 1,N6-ethenoadenine inosine or hypoxanthine and the nucleobases may be removed from these nucleotides using Human Alkyladenine DNA Glycosylase (hAAG). The polynucleotides may be modified to include uracil and the nucleobases removed with Uracil-DNA Glycosylase (UDG). The modified bases may, for example, be 2'-O-

Methyl (2'OMe) and/or 2'-fluoro bases. The complementary or universal strand may be present in an adapter, such as a Y adapter for characterising the selected polynucleotides using a transmembrane pore, e.g. the further polynucleotide may be an adapter, such as a Y adapter.

A site for attaching a molecule, may for example, be a single stranded DNA section that can bind, when exposed, to a single stranded DNA binding protein (SSB), such as the *E. coli* single stranded binding protein.

The further polynucleotide or other molecule may, for example, be tagged, allow ligation to the polynucleotides to which the strand is hybridised, or conversely to prevent ligation to the polynucleotides to which the strand is hybridised, allow digestion, or conversely prevent digestion. The ligation may be direct ligation, for example using a ligase or indirect ligation such as using click chemistry.

The adapter may, in addition to or instead of a tag, comprise a hidden site that can be ligated to another strand when the site becomes exposed. The adapter may, in addition to or instead of a tag, comprise an exposed site for attaching a further polynucleotide that can be ligated to another strand.

The adapter may, in addition to or instead of a tag, comprise a hidden site that allows digestion of the strand when it becomes exposed. The adapter may, in addition to or instead of a tag, comprise an exposed site that allows digestion of the strand when it becomes exposed. The adapter may, in addition to or instead of a tag, contain a chemical group suitable for click chemistry attachment that is hidden or exposed.

The adapter may be single stranded and/or double stranded. The adapter may, for example, contain both single stranded and double stranded sections. The adapter may attach to one strand, or preferably to both strands of a double stranded polynucleotide. An adapter may be attached to one or both ends of each of the multiple polynucleotides.

Preferably, when the selected nucleotides are modified with a sequencing adapter, (i) a nucleic acid handling enzyme and/or (ii) a membrane anchor or a transmembrane pore anchor may be attached to the sequencing adapter.

Nucleic Acid Handling Enzyme

A nucleic acid handling enzyme may be attached to the sequencing adapter for example in order to promote characterisation of the selected polynucleotides in accordance with the methods disclosed herein. For example, in methods which comprise contacting the selected polynucleotides with a transmembrane pore, the nucleic acid handling enzyme may facilitate interaction of the selected polynucleotides with the pore.

The nucleic acid handling enzyme may be any protein that is capable of binding to a polynucleotide and processing the polynucleotide. In processing the polynucleotide, the nucleic acid handling enzyme moves along the polynucleotide. The direction of movement of the enzyme is consistent. Consistent movement means that the enzyme moves from the 5' end to the 3' end of the polynucleotide or vice versa. The enzyme may modify the polynucleotide as it processes it. It is not essential that modification of the polynucleotide occurs. Therefore, the nucleic acid handling enzyme may be a modified enzyme that retains its ability to move along a polynucleotide.

The nucleic acid handling enzyme may be, for example, a translocase, a helicase, a polymerase or an exonuclease.

The nucleic acid handling enzyme may move along a single stranded polynucleotide, such as single stranded DNA or single stranded RNA, or may move along a double stranded polynucleotide such as double stranded DNA or a DNA/RNA hybrid. For example, helicases or translocases that act on either single stranded or double stranded DNA may be used.

The helicase may, for example, be a member of superfamily 1 or superfamily 2. The helicase is preferably a member of one of the following families: Pif1-like, Upf1-like, UvrD/Rep, Ski-like, Rad3/XPD, NS3/NPH-II, DEAD, DEAH/RHA, RecG-like, REcQ-like, TIR-like, Swi/Snf-like and Rig-I-like. The first three of those families are in superfamily 1 and the second ten families are in superfamily 2. The helicase is more preferably a member of one of the following subfamilies: RecD, Upf1 (RNA), PcrA, Rep, UvrD, Hel308, Mtr4 (RNA), XPD, NS3 (RNA), Mss116 (RNA), Prp43 (RNA), RecG, RecQ, TIR, *RapA* and Hef (RNA). The first five of those subfamilies are in superfamily 1 and the second eleven subfamilies are in superfamily 2. Members of the Upf1, Mtr4, NS3, Mss116, Prp43 and Hef subfamilies are RNA helicases. Members of the other subfamilies are DNA helicases.

The helicase may be a multimeric or oligomeric helicase. In other words, the helicase may need to form a multimer or an oligomer, such as a dimer, to function. In such embodiments, the two or more parts cannot be on different monomers. The helicase is preferably monomeric. In other words, the helicase preferably does not need to form a multimer or an oligomer, such as a dimer, to function. For example, Hel308, RecD, TraI and XPD helicases are all monomeric helicases. These are discussed in more detail below. Methods for determining whether or not a helicase is oligomeric/multimeric or monomeric are known in the art. For instance, the kinetics of radiolabelled or fluorescently-labelled polynucleotide unwinding using the helicase can be examined. Alternatively, the helicase can be analysed using size exclusion chromatography.

Monomeric helicases may comprise several domains attached together. For instance, TraI helicases and TraI subgroup helicases may contain two RecD helicase domains, a relaxase domain and a C-terminal domain. The domains typically form a monomeric helicase that is capable of functioning without forming oligomers.

Particular examples of suitable helicases include Hel308, NS3, Dda, UvrD, Rep, PcrA, Pif1 and TraI. These helicases typically work on single stranded DNA. Examples of helicases that can move along both strands of a double stranded DNA include FtfK and hexameric enzyme complexes, or multisubunit complexes such as RecBCD.

The helicase may, for example, be any of the helicases, modified helicases or helicase constructs disclosed in WO 2013/057495, WO 2013/098562, WO2013098561, WO 2014/013260, WO 2014/013259, WO 2014/013262 and WO/2015/055981. The Hel308 helicase preferably comprises any one or more of the modifications disclosed in WO 2014/013260. The Dda helicase preferably comprises any one or more of the modifications disclosed in WO 2015/055981 and/or WO 2016/055777.

The nucleic acid handling enzyme may be a polymerase. A polymerase will typically synthesize a complementary polynucleotide strand as it moves along a polynucleotide. Otherwise, a polymerase may be used in a similar manner to a translocase. The polymerase may be a modified polymerase which retains its ability to move along a polynucleotide, but which does not synthesize a complementary strand. The polymerase may, for example, be PyroPhage® 3173 DNA Polymerase (which is commercially available from Lucigen® Corporation), SD Polymerase (commercially available from Bioron®) or variants thereof. The enzyme is preferably Phi29 DNA polymerase or a variant thereof.

Synthesis of a complementary strand may be advantageous in that it increases the amount of polynucleotide. Increasing the amount of polynucleotide may improve sensitivity of any subsequent assay using the polynucleotide selected by the method. Where the polynucleotide contains modified bases, the polymerase may be used to synthesize a complementary strand that contains normal bases, which can also be advantageous for subsequent assays using the polynucleotide.

Using a polymerase may have the advantage that it can be used to distinguish a damaged polynucleotide from an undamaged polynucleotide. For example, the polymerase may be unable to pass through an abasic nucleotide in DNA or through thymadine dimers. Accordingly, a method using a polymerase may be used to separate damaged polynucleotides from undamaged polynucleotides.

The nucleic acid handling enzyme may be an exonuclease. An exonuclease typically digest the polynucleotide as it moves along it. The exonuclease typically cleaves one strand of a double stranded polynucleotide to form individual nucleotides or shorter chains of nucleotides, such as di- or tri-nucleotides. Where an exonuclease is used, the polynucleotides which are ultimately selected are the undigested strands of double stranded polynucleotide, or polynucleotides in which one of the strands is partially digested and the other strand is intact. Any exonuclease enzyme may be used in the method. Preferred enzymes for use in the method include exonuclease III enzyme from *E. coli*, exonuclease I from *E. coli*, bacteriophage lambda exonuclease and enzymes derived from exonuclease III enzyme from *E. coli*, exonuclease I from *E. coli*, bacteriophage lambda exonuclease. An enzyme derived from one of these exonucleases preferably comprises the domains responsible for binding to the nucleic acid and for digesting the nucleic acid (catalytic domain).

The nucleic acid handling enzyme is preferably one that is able to process long polynucleotide strands without unbinding from the polynucleotide. Typically, the nucleic acid handling enzyme is capable of moving along a polynucleotide strand of from 500 nucleotide base pairs up to 250 million nucleotide base pairs, such as from 1,000, 2,000, 5,000, 10,000, 50,000 or 100,000 nucleotide base pairs up to 200 million, 100 million, 10 million or 1 million nucleotide base pairs.

The enzyme may be modified or unmodified. The enzyme may be modified to form a closed-complex. A closed-complex is an enzyme in which the polynucleotide binding site is modified such that the enzyme is closed around the polynucleotide in such a way that the enzyme does not fall off the polynucleotide other than when it reaches the end of the polynucleotide. Examples of suitable closed-complex enzymes and methods for modifying enzymes to produce closed complexes are disclosed in, for example, WO 2014/013260 and WO 2015/055981.

Where the nucleic acid handling enzyme is an unmodified polymerase, the enzyme is typically capable of moving along a polynucleotide of up to 30 kb. The distance of movement may be increased by modifying the polymerase to close an opening from which the polynucleotide is able to unbind when the enzyme is part way along the polynucleotide. For such a modified polymerase, the longer polynucleotide lengths specified above may be processed by the polymerase.

Anchor

A membrane anchor or a transmembrane pore anchor may be attached to the sequencing adapter for example in order to promote characterisation of the selected polynucleotides in accordance with the methods disclosed herein. For example, in methods which comprise contacting the selected polynucleotides with a transmembrane pore, a membrane anchor or transmembrane pore anchor may promote localisation of the selected polynucleotides around the transmembrane pore.

The anchor may be a polypeptide anchor and/or a hydrophobic anchor that can be inserted into the membrane. The hydrophobic anchor is preferably a lipid, fatty acid, sterol, carbon nanotube, polypeptide, protein or amino acid, for example cholesterol, palmitate or tocopherol. The anchor may comprise thiol, biotin or a surfactant.

In one aspect the anchor may be biotin (for binding to streptavidin), amylose (for binding to maltose binding protein or a fusion protein), Ni-NTA (for binding to polyhistidine or poly-histidine tagged proteins) or peptides (such as an antigen).

The anchor may comprise a linker, or 2, 3, 4 or more linkers. Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The adapter may hybridise to a complementary sequence on a circular polynucleotide linker. The one or more anchors or one or more linkers may comprise a component that can be cut or broken down, such as a restriction site or a photolabile group. The linker may be functionalised with maleimide groups to attach to cysteine residues in proteins. Suitable linkers are described in WO 2010/086602.

The anchor is preferably cholesterol or a fatty acyl chain. For example, any fatty acyl chain having a length of from 6 to 30 carbon atom, such as hexadecanoic acid, may be used.

Examples of suitable anchors and methods of attaching anchors to adapters are disclosed in WO 2012/164270 and WO 2015/150786.

Transmembrane Pore

The methods provided herein preferably further comprise bringing the selected polynucleotides into contact with a transmembrane pore. More preferably the methods comprise contacting the selected polynucleotides with a transmembrane pore and thereby characterising the selected polynucleotides. Characterisation of the selected polynucleotides can be achieved as described herein.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the methods provided herein. The pore may be biological or artificial. Suitable pores include, but are not limited to, protein pores, polynucleotide pores and solid state pores. The pore may be a DNA origami pore (Langecker et al., Science, 2012; 338:932-936). Suitable DNA origami pores are disclosed in WO2013/083983.

The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the methods provided herein, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane cx-helix bundle or channel.

The barrel or channel of the transmembrane protein pore typically comprises amino acids that facilitate interaction with an analyte, such as a nucleotide, polynucleotide or nucleic acid. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the methods provided herein can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and a outer membrane proteins, such as WZA and ClyA toxin.

The transmembrane pore may be derived from or based on Msp, α-hemolysin (α-HL), lysenin, CsgG, ClyA, Sp1 and haemolytic protein fragaceatoxin C (FraC).

The transmembrane protein pore is preferably derived from CsgG, more preferably from CsgG from *E. coli* Str. K-12 substr. MC4100. Such a pore will be oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others. Suitable pores derived from CsgG are disclosed in WO 2016/034591.

The transmembrane pore is preferably derived from lysenin. Suitable pores derived from lysenin are disclosed in WO 2013/153359.

The transmembrane pore is preferably derived from or based on α-hemolysin (α-HL). The wild type α-hemolysin pore is formed of 7 identical monomers or sub-units (i.e., it is heptameric). An α-hemolysin pore may be α-hemolysin-NN or a variant thereof. The variant preferably comprises N residues at positions E111 and K147.

The transmembrane protein pore is preferably derived from Msp, more preferably from MspA. Suitable pores derived from MspA are disclosed in WO 2012/107778.

The transmembrane pore is preferably a variant of Msp, «-hemolysin (α-HL), lysenin, CsgG, ClyA, Sp1 or haemolytic protein fragaceatoxin C (FraC).

A variant of a given ("reference") polypeptide is a polypeptide that has an amino acid sequence which varies from that of the reference polypeptide and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and WO 2006/100484.

Over the entire length of a given reference sequence, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid reference sequence over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (http://www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

Amino acid substitutions may be made to the sequences of ppts such as Msp, α-hemolysin (α-HL), lysenin, CsgG, ClyA, Sp1 and haemolytic protein fragaceatoxin C (FraC). For example up to 1, 2, 3, 4, 5, 10, 20 or 30 substitutions may be made. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Braha et al. (1997) Chem Biol. 4 (7): 497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, NY.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.
Characterisation A method of characterising a polynucleotide is provided. The characterisation method comprises:

i) carrying out a method as described herein;

ii) contacting a transmembrane pore with the selected polynucleotides;

iii) applying a potential difference across the transmembrane pore; and iv) taking one or more measurements which are indicative of one or more characteristics of a polynucleotide moving with respect to the transmembrane pore and thereby characterising the polynucleotide.

The one or more characteristics may be selected from (i) the length of the polynucleotide, (ii) the identity of the polynucleotide, (iii) the sequence of the polynucleotide, (iv) the secondary structure of the polynucleotide and (v) whether or not the polynucleotide is modified. Preferably, the one or more characteristics of the polynucleotide include the sequence of the polynucleotide.

The characterisation method typically comprises measuring the current passing through the transmembrane pore as the polynucleotide moves with respect to the transmembrane pore.

Electrical measurements may be made using standard single channel recording equipment as describe in Stoddart, D. S., et al., (2009), *Proceedings of the National Academy of Sciences of the United States of America* 106, p 7702-7707, Lieberman K R et al, J Am Chem Soc. 2010; 132 (50): 17961-72, and International Application WO-2000/28312. Alternatively, electrical measurements may be made using a multi-channel system, for example as described in WO 2009/077734 and WO 2011/067559.

The characterisation methods may be carried out using any apparatus that is suitable for investigating a membrane/pore system in which a pore is inserted into a membrane. The characterisation method may be carried out using any apparatus that is suitable for transmembrane pore sensing. For example, the apparatus may comprise a chamber comprising an aqueous solution and a barrier that separates the chamber into two sections. The barrier may have an aperture in which a membrane containing a transmembrane pore is formed. Transmembrane pores are described herein.

The characterisation methods may be carried out using the apparatus described in WO 2008/102120, WO 2010/122293 or WO 00/28312.

The characterisation methods may involve measuring the ion current flow through the pore, typically by measurement of a current. Alternatively, the ion flow through the pore may be measured optically, such as disclosed by Heron et al: J. Am. Chem. Soc. 9 Vol. 131, No. 5, 2009. Therefore the apparatus may also comprise an electrical circuit capable of applying a potential and measuring an electrical signal across the membrane and pore. The characterisation methods may be carried out using a patch clamp or a voltage clamp. The characterisation methods preferably involve the use of a voltage clamp.

The characterisation methods may be carried out on a silicon-based array of wells where each array comprises 128, 256, 512, 1024, 2000, 3000, 4000, 6000, 10000, 12000, 15000 or more wells.

The characterisation methods may involve the measuring of a current flowing through the pore. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The characterisation methods are typically carried out in the presence of any charge carriers, such as metal salts, for example alkali metal salts, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt may be an alkaline earth metal salt such as calcium chloride (CaCl2). The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The characterisation method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of binding/no binding to be identified against the background of normal current fluctuations.

The characterisation methods are typically carried out in the presence of a buffer. In the exemplary apparatus discussed above, the buffer is present in the aqueous solution in the chamber. Any suitable buffer may be used. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The characterisation methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The characterisation methods are typically carried out at room temperature. The characterisation methods are optionally carried out at a temperature that supports enzyme function, such as about 37° C.

The inventors have found that when the selection methods are applied to select polynucleotides from a sample comprising a mixture of polynucleotides, the signal quality recorded when characterising the selected polynucleotides is improved relative to the signal quality of the sample of polynucleotides. Improved signal is typically observed as increased read lengths. The read length of a polynucleotide is determined by various factors and includes the homogeneity of the sample. The read length of a sample can be represented by parameters, for example the N50 value or the N75 value. For a given set of measurements, 50% of measurements are longer than the N50 value and 50% of measurements are shorter than the N50 value. Similarly, 75% of measurements are longer than the N75 value and 25% of measurements of shorter than then N75 value. The methods beneficially allow the N50 and N75 values observed for samples of polynucleotides to be increased. Accordingly, preferably, in the selection methods, the average read length of the selected polynucleotides is longer than the average read length of the initial sample.

Kits

Further provided is a kit for separating polynucleotides, the kit comprising:

a filter; and a condensing medium;

and optionally further comprising an extending medium.

Preferably, the filter is a filter as described herein. Preferably the condensing medium is a condensing medium as described herein. If present, preferably the extending medium is an extending medium as described herein Preferably, the kit further comprises one or more of:

a sequencing adapter as described herein; and/or a membrane anchor or a transmembrane pore anchor as described herein; and/or a nucleic acid handling enzyme as described herein; and/or fuel and/or cofactor for a nucleic acid handling enzyme; and/or wash solution, which does not comprise fuel and/or cofactor for a nucleic acid handling enzyme.

The activity of a polynucleotide-handling enzyme can be controlled by adding or removing fuel and/or co-enzymes/co-factors. Fuel is typically free nucleotides or free nucleotide analogues. The free nucleotides may be one or more of, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the polynucleotide binding protein to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Wash solutions are free of fuel and/or cofactor for a nucleic acid handling enzyme and are typically sterile and/or free of enzymes that can degrade polynucleotides such as DNase and/or DNase. A wash solution is preferably an aqueous solution such as a buffer solution or DNase- and RNase-free water.

The following Examples illustrate the invention. The Examples do not, however, limit the invention in any way.

EXAMPLES

Example 1

This example demonstrates that the methods provided herein can be used to size select DNA of a desired size from a mixed library containing dsDNA fragments ranging in size.

A mixed library containing dsDNA fragments ranging in size from 100 bp to 48 kbp was prepared and applied to a range of filters with increasing pore size and in two different buffers. By control of the pore size and buffer solutions used, it was possible to select desired polynucleotides from the mixed library in accordance with the methods provided herein.

Figure 2:
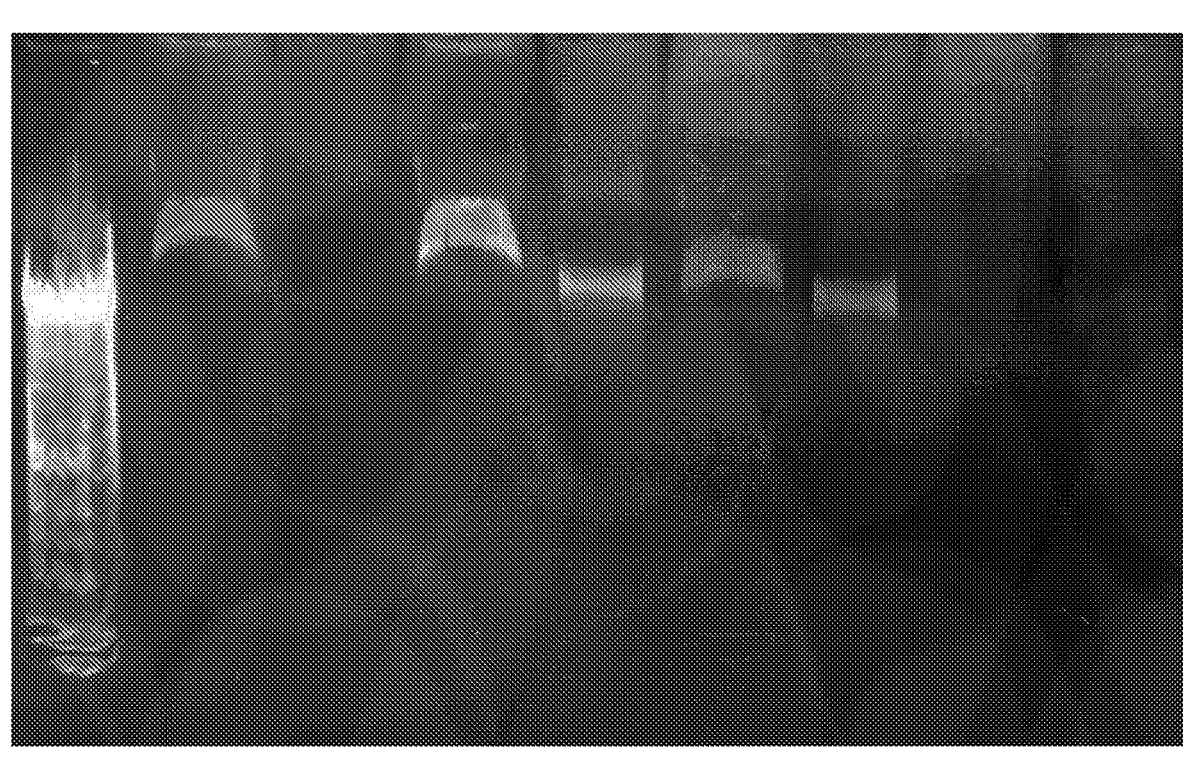
FIG. 2 shows control (lane 1) and size-selected fractions (lanes 2-9) of DNA analysed on a 0.75% lithium acetate agarose gel, run for 15 minutes at 250 V and visualised using SYBR gold. Results are described in Example 1.

Results are shown in FIG. 2. This Figure shows a 0.75% lithium acetate agarose gel, run for 15 minutes at 250 V and visualised using SYBR gold in accordance with standard protocols. The gel was loaded with various DNA fractions from the mixed library selected in accordance with the methods provided herein. Fractions loaded on the gel were as follows:

Lane 1—Control of 1 µg 1 kb DNA ladder (NEB) mixed with 1 µg Bacteriophage lambda DNA (NEB).

Lane 2—1 µg 1 kb DNA ladder mixed with 1 µg Bacteriophage lambda DNA was incubated in DNA condensing buffer (60 mg/ml PEG 6000, 600 mM NaCl) and applied to a 0.1 µm nylon filter (Acrodisc) and eluted with 50 µl TE (10 mM Tris-HCl (pH 8.0)) buffer.

Lane 3—1 µg 1 kb DNA ladder mixed with 1 µg Bacteriophage lambda DNA was incubated in TE (10 mM Tris-HCl (pH 8.0)) and applied to a 0.1 µm nylon filter (Acrodisc) and eluted with 50 µl TE (10 mM Tris-HCl (pH 8.0)) buffer.

Lane 4—1 µg 1 kb DNA ladder mixed with 1 µg Bacteriophage lambda DNA was incubated in DNA condensing buffer (60 mg/ml PEG 6000, 600 mM NaCl) and applied to a 0.2 µm nylon filter (Acrodisc) and eluted with 50 µl TE (10 mM Tris-HCl (pH 8.0)) buffer.

Lane 5—1 µg 1 kb DNA ladder mixed with 1 µg Bacteriophage lambda DNA was incubated in TE (10 mM Tris-HCl (pH 8.0)) and applied to a 0.2 µm nylon filter (Acrodisc) and eluted with 50 µl TE (10 mM Tris-HCl (pH 8.0)) buffer.

Lane 6—1 µg 1 kb DNA ladder mixed with 1 µg Bacteriophage lambda DNA was incubated in DNA condensing buffer (60 mg/ml PEG 6000, 600 mM NaCl) and applied to a 0.45 µm nylon filter (Acrodisc) and eluted with 50 µl TE (10 mM Tris-HCl (pH 8.0)) buffer.

Lane 7—1 µg 1 kb DNA ladder mixed with 1 µg Bacteriophage lambda DNA was incubated in TE (10 mM Tris-HCl (pH 8.0)) and applied to a 0.45 µm nylon filter (Acrodisc) and eluted with 50 µl TE (10 mM Tris-HCl (pH 8.0)) buffer.

Lane 8—1 µg 1 kb DNA ladder mixed with 1 µg Bacteriophage lambda DNA was incubated in DNA condensing buffer (60 mg/ml PEG 6000, 600 mM NaCl) and applied to a 5 µm nylon filter (Acrodisc) and eluted with 50 µl TE (10 mM Tris-HCl (pH 8.0)) buffer.

Lane 9—1 µg 1 kb DNA ladder mixed with 1 µg Bacteriophage lambda DNA was incubated in TE (10 mM Tris-HCl (pH 8.0)) and applied to a 5 µm nylon filter (Acrodisc) and eluted with 50 µl TE (10 mM Tris-HCl (pH 8.0)) buffer.

The fractions loaded on the gel are thus summarised as follows:

| Lane | Incubation Buffer | Eluting Buffer | Filter Pore Size |
|---|---|---|---|
| 2 | DNA condensing buffer | TE buffer | 0.1 µm |
| 3 | TE buffer | TE buffer | |
| 4 | DNA condensing buffer | TE buffer | 0.2 µm |
| 5 | TE buffer | TE buffer | |
| 6 | DNA condensing buffer | TE buffer | 0.45 µm |
| 7 | TE buffer | TE buffer | |
| 8 | DNA condensing buffer | TE buffer | 5 µm |
| 9 | TE buffer | TE buffer | |

-continued

| Lane | Incubation Buffer | Eluting Buffer | Filter Pore Size |
|---|---|---|---|

DNA condensing buffer = (60 mg/ml PEG 6000, 600 mM NaCl)
TE = 10 mM Tris-HCl (pH 8.0)

For each sample the 2 µg of DNA was incubated/mixed in 500 µL of the indicated incubation buffer (for approx. 1 minute) and subsequently applied to a filter having the indicated pore size using a 1 mL syringe, then washed with 1000 µL of fresh buffer, followed by 1 mL of air to dry the filter. DNA was eluted by drawing 50 µL TE buffer back through the filter to re-suspend the sample. It can be seen that all of the filters effectively select DNA fragments over 10 kbp with the 0.2 µm filters recovering the greatest quantity of DNA and the 5 µm sized filters recovering little to no DNA.

Benefits of the DNA condensing buffer can be seen for example in the 0.2 µm pore size buffer comparison (FIG. 2, lanes 4 and 5). DNA in a globular form is resistant to shear forces and so does not fragment when applied to the filter. Accordingly, a discrete band for selected DNA (ca. 10 kbp) is observed in lane 4. By contrast, when no condensing buffer is used, the DNA does not adopt a globular form and fragments when applied to the filter, as evidenced by the smear below the main band in lane 5 of FIG. 2.

Example 2

This Example shows that DNA size-selected in accordance with the methods provided herein yields increased read lengths when characterised by nanopore sequencing.

A sample of human DNA (Human Male Genomic, Promega) was sequenced both with and without size selection using Oxford Nanopore Technologies Ltd. MinION sequencer. Two samples were prepared according to a standard library protocol (SQK-LSK108, Oxford Nanopore Technologies Ltd; https://store.nanoporetech.com/ligation-sequencing-kit-1d.html. In brief, this protocol involves DNA ends being repaired and dA-tailed using the NEBNext End Repair/dA-tailing module, and then sequencing adapters being ligated onto the prepared ends. One sample was subjected to size selection in accordance with the methods provided herein by incubating/mixing the sample with DNA condensing medium for approx. 1 minute (60 mg/ml PEG 6000, 600 mM NaCl) prior to the ligation of the sequencing adaptors. (Filter size 0.2 µm). The other sample was not subjected to size selection prior to the ligation of the sequencing adaptors.

Figure 3:
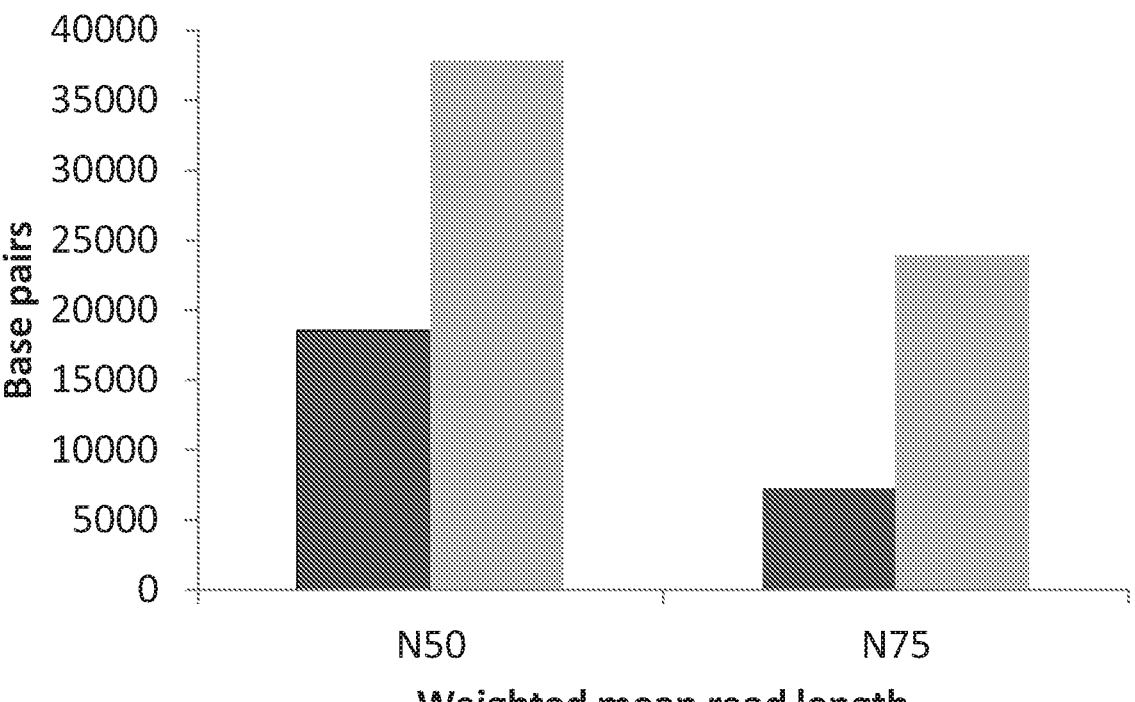
FIG. 3 shows N50 and N75 values (x axis) of weighted mean read lengths in base pairs (y axis) determined from sequencing human male genomic DNA. Dark grey bars represent data obtained from control DNA which was not subjected to size selection in accordance with the methods provided herein. Light grey bars represent data obtained from DNA which was size selected in accordance with the methods provided herein. Results are described in Example 2.

Both samples were sequenced on separate flowcells, and the read lengths of the libraries compared. Results are shown in FIG. 3.

The N50 value of a sequenced library is the size at which 50% of the reads are larger than the value and 50% of the reads are smaller than the value. Similarly, the N75 value of a sequenced library is the size at which 75% of the reads are larger than the value and 25% of the reads are smaller than the value. It can be seen from FIG. 3 that the N50 of the sample which was post size selected is increased from 18504 bp to 37846 bp relative to the non-size selected control. Similarly, the N75 value of the sample is increased from 7261 bp to 23956 bp respectively after size selection. These results demonstrate that DNA size-selected in accordance with the methods provided herein yields increased read lengths when characterised by nanopore sequencing.

Example 3

This Example further shows that DNA size-selected in accordance with the methods provided herein yields increased read lengths when characterised by nanopore sequencing.

A sample of human DNA (Human Male Genomic, Promega) was sequenced both with and without size selection using Oxford Nanopore Technologies Ltd. MinION sequencer. Samples were prepared as described in Example 2. Accordingly, one sample was subjected to size selection in accordance with the methods provided herein by incubating the sample with DNA condensing medium prior to the ligation of the sequencing adaptors. The other sample was not subjected to size selection prior to the ligation of the sequencing adaptors. Both samples were sequenced on separate flowcells, and the read lengths of the libraries compared. Results are shown in FIG. 4.

Figure 4:
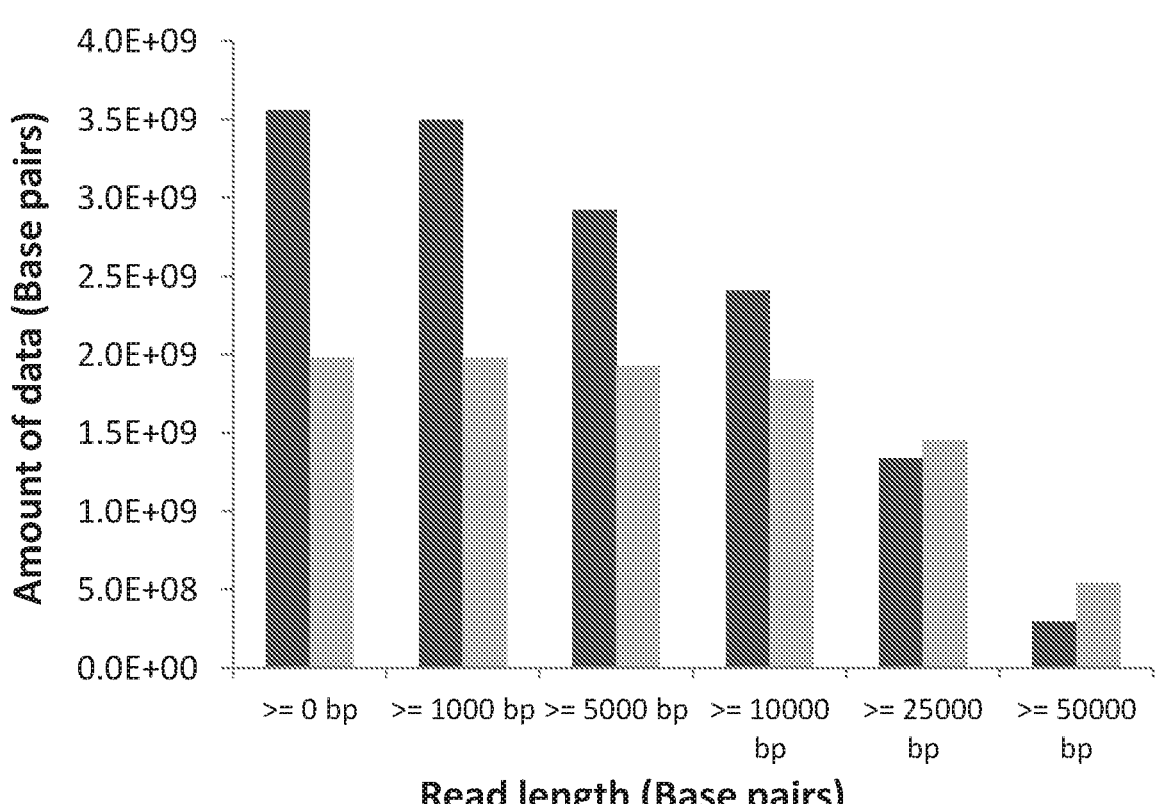
FIG. 4 shows average read lengths recorded from sequencing human male genomic DNA. Bins representing average read lengths in base pairs (x axis) are plotted against the number of hits in each bin (i.e. the amount of data recorded; y axis). Dark grey bars represent data obtained from control DNA which was not subjected to size selection in accordance with the methods provided herein. Light grey bars represent data obtained from DNA which was size selected in accordance with the methods provided herein. Results are described in Example 3.

It can be seen from the results shown in FIG. 4 that more of the shorter fragments are removed with size selection with the size selected sample producing slightly more desired reads over 25 kbp and many more over 50 kbp.

Example 4

This Example further shows that DNA size-selected in accordance with the methods provided herein yields increased read lengths when characterised by nanopore sequencing.

A sample of human DNA (cell line GM12878) was sequenced both with and without size selection using Oxford Nanopore Technologies Ltd. MinION sequencer. Samples were prepared, size selected and read lengths determined as described in Example 2.

Figure 5:
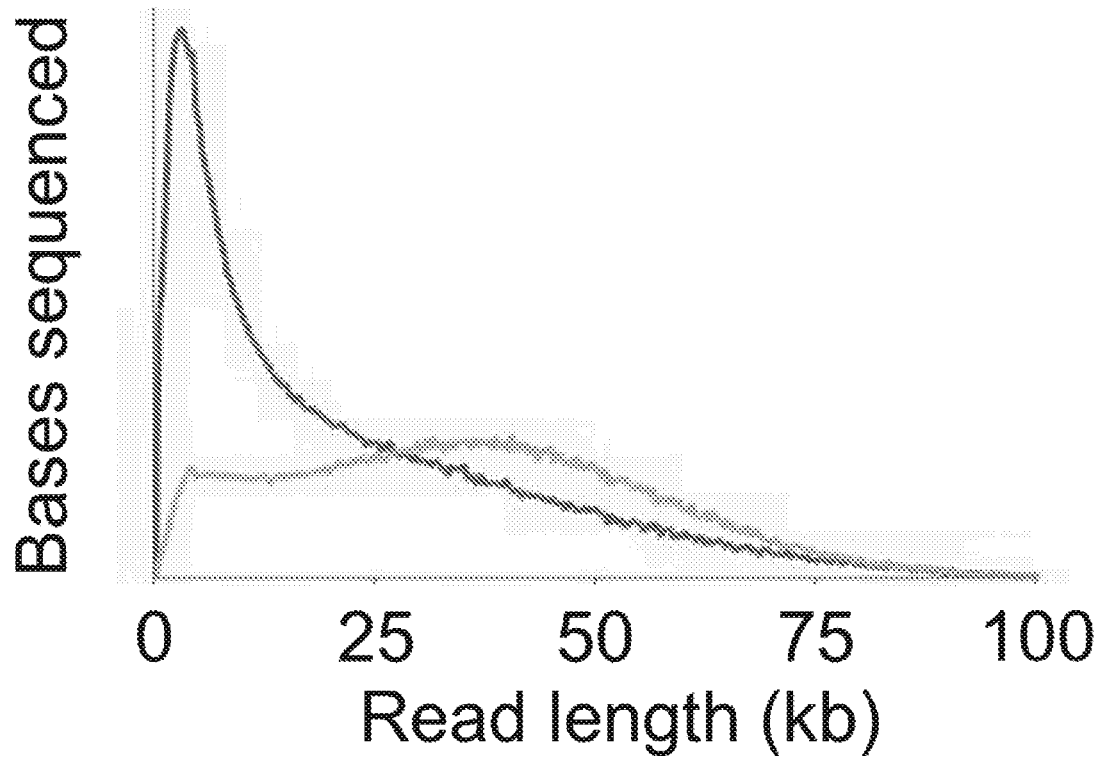
FIG. 5 shows average read lengths recorded from sequencing human DNA (GM12878). The average read length in base pairs (x axis) is plotted against the amount of data recorded; y axis). Dark grey: data obtained from control DNA which was not subjected to size selection in accordance with the methods provided herein. Light grey: data obtained from DNA which was size selected in accordance with the methods provided herein. Results are described in Example 4.

The read lengths of the size-selected and non-size-selected samples were compared. Results are shown in FIG. 5 (dark grey=non-selected; light grey=size selected in accordance with the methods disclosed herein). It can be seen that more of the shorter fragments are removed with size selection. The N50 value for the size-selected DNA is significantly higher than the corresponding N50 value for the non-size-selected DNA. Similarly, the N75 value of the sample is increased after size selection. Size selection results in significantly increased desired reads over ca. 25 kb and almost twice as many desired reads of ca. 50 kb.

The invention claimed is:

1. A method comprising:
   (i) providing a sample comprising a mixture of polynucleotides and contacting the sample with a condensing medium, the condensing medium comprising about 20 mg/ml to about 150 mg/ml of a hydrophilic polymer and having a salt concentration from 0.1 M to 1 M, such that the polynucleotides in the sample adopt a globular form;
      wherein contacting the sample with a condensing medium does not precipitate the polynucleotides in the sample;
   (ii) filtering the sample through a filter such that polynucleotides retained by the filter are selected polynucleotides and polynucleotides passing through the filter are unselected polynucleotides, wherein the selected polynucleotides are longer than unselected polynucleotides, thereby selecting polynucleotides based on the size of the polynucleotides in the globular form;

(iii) processing the selected polynucleotides such that the selected polynucleotides adopt a non-globular form, wherein the processing comprises contacting the selected polynucleotides with an extending medium; and
   (iv) sequencing the selected polynucleotides with a read length of at least about 25000 base pairs.

2. The method of claim 1, wherein the non-globular form is an extended form.

3. The method of claim 1, wherein the globular form is a condensed form wherein the polynucleotides are resistant to shear.

4. The method of claim 1, wherein the filter is a membrane filter.

5. The method of claim 1, wherein the filter has a pore size of from about 0.01 μm to about 100 μm.

6. The method of claim 1, wherein:
   (a) the hydrophilic polymer is a polyether or a polysaccharide having a molecular weight of from 2000 Da to 12000 Da; and/or
   (b) the condensing medium comprises a group (I) or group (II) metal salt.

7. The method of claim 1, wherein the concentration of salt in the extending medium is lower than the concentration of salt in the condensing medium, and wherein the concentration of polymer in the extending medium is lower than the concentration of polymer in the condensing medium.

8. The method of claim 1, wherein the extending medium elutes the selected polynucleotides from the filter.

9. The method of claim 1, wherein the polynucleotides are DNA, RNA or DNA/RNA hybrids.

10. The method of claim 1, wherein the sample comprises:
    (a) products of a PCR reaction; and/or
    (b) a DNA library; and/or
    (c) genomic DNA; and/or
    (d) products of an endonuclease digestion.

11. The method of claim 1, wherein prior to the sequencing of step (iv), the method further comprises attaching a sequencing adapter to the selected polynucleotides, wherein the sequencing adapter is attached to:
    (a) a nucleic acid handling enzyme, and/or
    (b) a membrane anchor and/or a transmembrane pore anchor; and
    wherein the sequencing of step (iv) comprises bringing the selected polynucleotides into contact with a transmembrane pore.

12. The method of claim 1, wherein the sequencing of step (iv) comprises:
    (1) contacting a transmembrane pore with the selected polynucleotides;
    (2) applying a potential difference across the transmembrane pore; and
    (3) taking one or more measurements as the selected polynucleotides move with respect to the transmembrane pore, thereby sequencing the selected polynucleotides.

13. The method of claim 4, wherein the membrane filter is a syringe filter.

14. The method of claim 6, wherein the hydrophilic polymer is polyethylene glycol and/or the metal salt is a metal halide.

15. The method of claim 1, wherein the polynucleotides are double stranded DNA.

* * * * *